United States Patent
Rakshit

(10) Patent No.: US 9,803,987 B2
(45) Date of Patent: Oct. 31, 2017

(54) PRESCRIPTION-BASED TRAVEL ROUTE RECOMMENDATION

(71) Applicant: International Business Machines Corporation, Armonk, NY (US)

(72) Inventor: Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 26 days.

(21) Appl. No.: 14/460,493

(22) Filed: Aug. 15, 2014

(65) Prior Publication Data

US 2014/0358422 A1 Dec. 4, 2014

Related U.S. Application Data

(63) Continuation of application No. 13/269,834, filed on Oct. 10, 2011, now Pat. No. 8,892,354.

(51) Int. Cl.
*G01C 21/20* (2006.01)
*G01C 21/34* (2006.01)
*G06F 19/00* (2011.01)

(52) U.S. Cl.
CPC .......... *G01C 21/3407* (2013.01); *G01C 21/20* (2013.01); *G01C 21/3484* (2013.01); *G06F 19/3481* (2013.01)

(58) Field of Classification Search
CPC ........................... G01C 21/3407; G01C 21/20; G01C 21/3484; G06F 19/3481

(Continued)

(56) References Cited

U.S. PATENT DOCUMENTS

| 6,028,553 A | 2/2000 | Oberstein |
| 7,072,840 B1 | 7/2006 | Mayaud |

(Continued)

FOREIGN PATENT DOCUMENTS

EP 0814448 A2 12/1997

OTHER PUBLICATIONS http://web.archive.org/web/20100316175307/http://www.exrx.net/Aerobic/AerobicComponents.html, Mar. 2010.*

(Continued)

*Primary Examiner* — Aaron L Troost
(74) *Attorney, Agent, or Firm* — Maeve M. Carpenter; Maxine L. Barasch; Koehane & D'Alessandro PLLC

(57) ABSTRACT

In general, embodiments of the present invention relate to prescription-based travel route recommendation. In a typical embodiment, a prescription related to a medical condition of a patient is received (e.g., electronically in a computer memory medium or the like). Among other things, the prescription typically comprises a set of criteria (e.g., route specifics such as topography/incline, mode of travel such as walking, running, cycling, etc.) for a desired travel route for the patient. Then, using global positioning satellite (GPS) technology or the like, the system will access/receive information corresponding to a geographical area associated with the patient. Using this information, a set of possible travel routes between a starting point and a destination within the geographical area will be determined. Then, by comparing the set of criteria to the information, at least one travel route will be identified from the possible travel routes for treating the medical condition. Once identified, one or more specific travel routes can be recommended (e.g., to the patient).

15 Claims, 4 Drawing Sheets

(58) Field of Classification Search
USPC .................................................. 701/410
See application file for complete search history.

(56) References Cited

U.S. PATENT DOCUMENTS

| | | | |
|---|---|---|---|
| 7,630,908 | B1 | 12/2009 | Amrien et al. |
| 7,680,595 | B2 | 3/2010 | Brinton et al. |
| 7,717,827 | B2 | 5/2010 | Kurunmaki et al. |
| 2002/0177945 | A1 | 11/2002 | Davies |
| 2005/0131737 | A1 | 6/2005 | Joseph et al. |
| 2008/0162393 | A1 | 7/2008 | Iliff |
| 2009/0309744 | A1 | 12/2009 | Fu et al. |
| 2010/0088023 | A1* | 4/2010 | Werner .............. A63B 24/0021 701/467 |
| 2010/0088095 | A1 | 4/2010 | John |
| 2010/0211304 | A1 | 8/2010 | Hwang et al. |
| 2010/0274579 | A1* | 10/2010 | Marten ................. G06F 19/325 705/2 |
| 2011/0066369 | A1* | 3/2011 | Klassen ................. G01C 21/20 701/465 |
| 2011/0092825 | A1 | 4/2011 | Gopinathan et al. |
| 2011/0112858 | A1 | 5/2011 | Neal |
| 2011/0213625 | A1 | 9/2011 | Joao |
| 2012/0101717 | A1 | 4/2012 | Zhang |
| 2012/0143497 | A1* | 6/2012 | Van Hende ........ G01C 21/3484 701/432 |
| 2012/0185164 | A1 | 7/2012 | McCoy et al. |
| 2012/0293315 | A1 | 11/2012 | Schunder et al. |

OTHER PUBLICATIONS

Premasudha, B.G., "Location Based Application for Accessing Emergency Pharmacy Services over the Mobile", International Conference Map Middle East—2007, Apr. 2-11, 2007 at Dubai, UAE, pp. 1-38.

"Health and Healing/Exercise/Walking Routes", University of Wisconsin School of Medicine and Public Health, one page. http://www.uwhealth.org/health-and-healing/exercise/walking-routes/27071.

Hedgecock, W. et al., "Dissemination and Presentation of High Resolution Air Pollution Data from Mobile Sensor Nodes", ACM SE 2010 Oxford, Mississippi, 6 pages.

Shriram, R. et al., "Web Based Counselling System with Electronic Prescription for Rural Area", Journal of Engineering Research and Studies, vol. II, Issue II, Apr.-Jun. 2011, pp. 143-148.

Zeadally, S. et al., "Design and Implementation of a Wireless Prescription System", Proceedings of the 37th Hawaii International Conference on System Sciences (2004), pp. 1-10.

"Ask a Doctor Online", http://www.i-medsource.com, 2 pages.

Aaron L. Troost, U.S. Office Action, U.S. Appl. No. 13/269,834, dated Oct. 23, 2012, 14 pages.

Aaron L. Troost, U.S. Final Office Action, U.S. Appl. No. 13/269,834, dated Apr. 10, 2013, 15 pages.

Aaron L. Troost, U.S. Office Action, U.S. Appl. No. 13/269,834, dated Jul. 17, 2013, 19 pages.

Aaron L. Troost, U.S. Office Action, U.S. Appl. No. 13/269,834, dated Jan. 13, 2014, 27 pages.

Aaron L. Troost, U.S. Notice of Allowance and Fee(s) Due, U.S. Appl. No. 13/269,834, dated Jul. 10, 2014, 28 pages.

* cited by examiner

PRESCRIPTION-BASED TRAVEL ROUTE RECOMMENDATION

CROSS-REFERENCE TO RELATED APPLICATIONS

The present patent document is a continuation of U.S. patent application Ser. No. 13/269,834, filed Oct. 10, 2011, entitled "PRESCRIPTION-BASED TRAVEL ROUTE RECOMMENDATION", the disclosure of which is incorporated herein by reference.

TECHNICAL FIELD

In general, embodiments of the present invention relate to electronic prescription processing. Specifically, embodiments of the present invention relate to a prescription-based travel route recommendation for the treatment of medical injuries, ailments, etc.

BACKGROUND OF THE INVENTION

As technology continues to advance, electronic medical processes continue to evolve. For example, today prescriptions can be electronically viewed and/or transmitted for fulfillment (e.g., assuming proper access control is provided). Moreover, various ailments and/or injuries often have a prescribed course of physical activity as treatment. For example, for diabetic patients, cardiac patients, etc., a medical professional may recommend exercise such as walking or jogging. Further, for patients with knees problems, a medical professional might suggest a flat topography (as opposed to a road with an incline).

Unfortunately, challenges can exist in identifying a specific action/course of treatment that addresses a recommended treatment plan. For example, a medical professional might not be aware of locations (and/or specifics thereof) where a physical course of treatment that matches his/her recommendations can be followed. That is, a medical professional may not be able to readily identify a travel/exercise route that meets a recommended course of exercise.

SUMMARY OF THE INVENTION

In general, embodiments of the present invention relate to prescription-based travel route recommendation. In a typical embodiment, a prescription related to a medical condition of a patient is received (e.g., electronically in a computer memory medium or the like). Among other things, the prescription typically comprises a set of criteria (e.g., route specifics such as topography/incline, mode of travel such as walking, running, cycling, etc.) for a desired travel route for the patient. Then, using global positioning satellite (GPS) technology or the like, the system will access/receive information corresponding to a geographical area associated with the patient. Using this information, a set of possible travel routes between a starting point and a destination within the geographical area will be determined. Then, by comparing the set of criteria to the information, at least one travel route will be identified from the possible travel routes for treating the medical condition. Once identified, one or more specific travel routes can be recommended (e.g., to the patient).

A first aspect of the present invention provides a computer-implemented method for a prescription-based travel route recommendation, comprising: receiving a prescription related to a medical condition of a patient in a computer memory medium, the prescription comprising a set of criteria for a desired travel route for the patient; receiving information corresponding to a geographical area associated with the patient; identifying a set of possible travel routes between a starting point and a destination within the geographical area based on the information; determining at least one travel route from the possible travel routes for treating the medical condition based on a comparison of the set of criteria to the information; and recommending the at least one travel route to the patient.

A second aspect of the present invention provides a system for a prescription-based travel route recommendation, comprising: a memory medium comprising instructions; a bus coupled to the memory medium; and a processor coupled to the bus that when executing the instructions causes the system to: receive a prescription related to a medical condition of a patient in a computer memory medium, the prescription comprising a set of criteria for a desired travel route for the patient; receive information corresponding to a geographical area associated with the patient; identify a set of possible travel routes between a starting point and a destination within the geographical area based on the information; determine at least one travel route from the possible travel routes for treating the medical condition based on a comparison of the set of criteria to the information; and recommend the at least one travel route to the patient.

A third aspect of the present invention provides a computer program product for prescription-based travel route recommendation, the computer program product comprising a computer readable storage media, and program instructions stored on the computer readable storage media, to: receive a prescription related to a medical condition of a patient in a computer memory medium, the prescription comprising a set of criteria for a desired travel route for the patient; receive information corresponding to a geographical area associated with the patient; identify a set of possible travel routes between a starting point and a destination within the geographical area based on the information; determine at least one travel route from the possible travel routes for treating the medical condition based on a comparison of the set of criteria to the information; and recommend the at least one travel route to the patient.

A fourth aspect of the present invention provides a method for deploying a system for a prescription-based travel route recommendation, comprising: providing a computer infrastructure being operable to: receive a prescription related to a medical condition of a patient in a computer memory medium, the prescription comprising a set of criteria for a desired travel route for the patient; receive information corresponding to a geographical area associated with the patient; identify a set of possible travel routes between a starting point and a destination within the geographical area based on the information; determine at least one travel route from the possible travel routes for treating the medical condition based on a comparison of the set of criteria to the information; and recommend the at least one travel route to the patient.

BRIEF DESCRIPTION OF THE DRAWINGS

These and other features of this invention will be more readily understood from the following detailed description of the various aspects of the invention taken in conjunction with the accompanying drawings in which.

Figure 1:
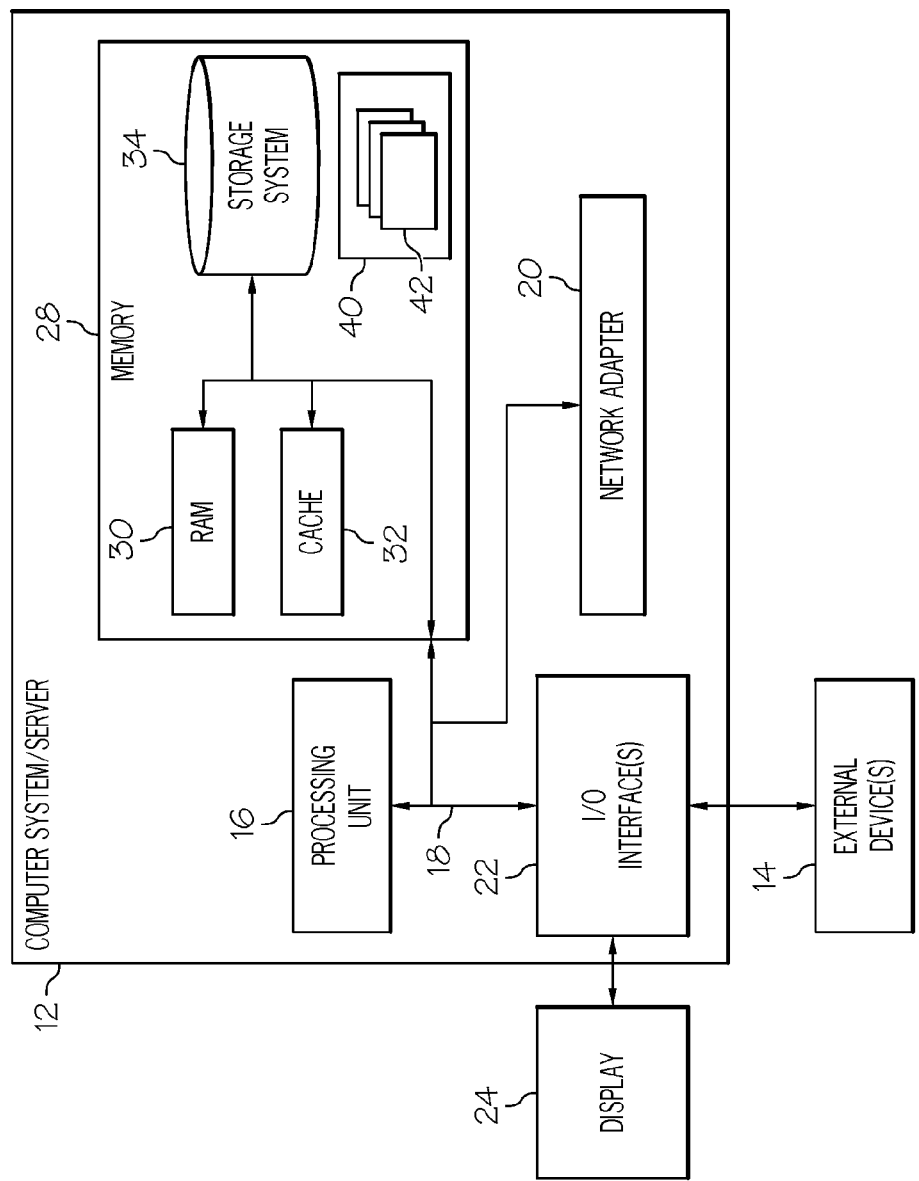
FIG. 1 depicts a computing node according to an embodiment of the present invention.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

Illustrative embodiments will now be described more fully herein with reference to the accompanying drawings, in which exemplary embodiments are shown. This disclosure may, however, be embodied in many different forms and should not be construed as limited to the exemplary embodiments set forth herein. Rather, these exemplary embodiments are provided so that this disclosure will be thorough and complete and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The word "set" is intended to mean a quantity of at least one. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

As mentioned above, embodiments of the present invention relate to prescription-based travel route recommendation. In a typical embodiment, a prescription related to a medical condition of a patient is received (e.g., electronically in a computer memory medium or the like). Among other things, the prescription typically comprises a set of criteria (e.g., route specifics such as topography/incline, mode of travel such as walking, running, cycling, etc.) for a desired travel route for the patient. Then, using global positioning satellite (GPS) technology or the like, the system will access/receive information corresponding to a geographical area associated with the patient. Using this information, a set of possible travel routes between a starting point and a destination within the geographical area will be determined. Then, by comparing the set of criteria to the information, at least one travel route will be identified from the possible travel routes for treating the medical condition. Once identified, one or more specific travel routes can be recommended (e.g., to the patient).

Referring now to FIG. 1, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10, there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, mobile devices, global positioning systems (GPS), GPS-enable devices, multiprocessor systems, microprocessor-based systems, set top boxes, programmable consumer electronics, network PCs, minicomputer systems, mainframe computer systems, and distributed computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on, that perform particular tasks or implement particular abstract data types. Computer system/server 12 may be practiced in distributed computing environments where tasks are performed by remote processing devices that are linked through a communications network. In a distributed computing environment, program modules may be located in both local and remote computer system storage media including memory storage devices.

As shown in FIG. 1, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM, or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

The embodiments of the invention may be implemented as a computer readable signal medium, which may include a propagated data signal with computer readable program code embodied therein (e.g., in baseband or as part of a carrier wave). Such a propagated signal may take any of a variety of forms including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium including, but not limited to, wireless, wireline, optical fiber cable, radio-frequency (RF), etc., or any suitable combination of the foregoing.

Travel route recommendation program/utility 40, having a set (at least one) of program modules 42, may be stored in memory 28 by way of example, and not limitation, as well as an operating system, one or more application programs, other program modules, and program data. In general, travel route recommendation program 40 performs the function of the present invention as described herein. For example, travel route recommendation program 40 will: receive a prescription related to a medical condition of a patient in a computer memory medium (e.g., comprising a set of criteria for a desired travel route for the patient); receive information corresponding to a geographical area associated with the patient; identify a set of possible travel routes between a starting point and a destination within the geographical area based on the information; determine at least one travel route from the possible travel routes for treating the medical condition based on a comparison of the set of criteria to the information; and/or recommend the at least one travel route to the patient. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a consumer to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
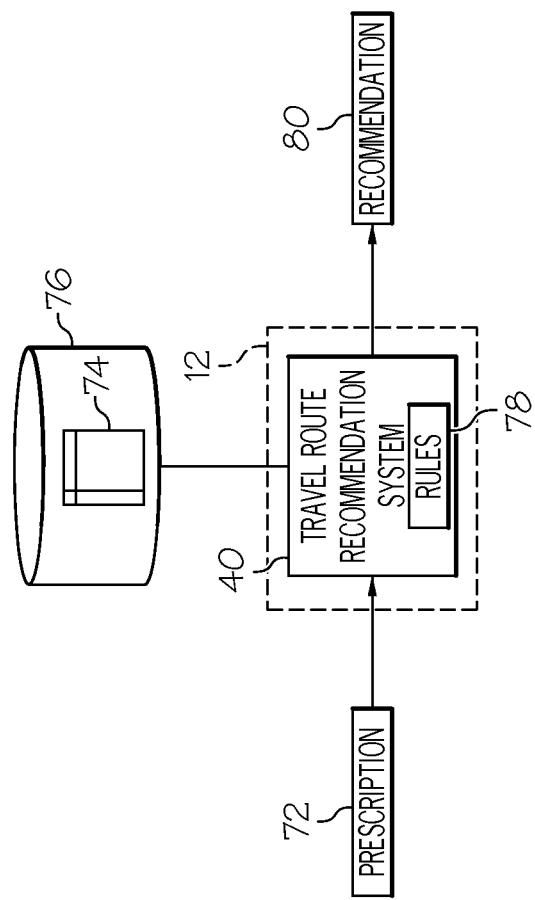
FIG. 2 depicts a system diagram according to an embodiment of the present invention.

Referring now to FIG. 2, a system diagram according to an embodiment of the present invention is shown. As depicted, a prescription 72 is typically received (e.g., electronically) by travel route recommendation program 40 (shown implemented on computer system/server 12) from a health care provider/system or the like. In general, prescription 72 will be stored in a computer storage medium or the like, such as memory 28 (FIG. 1) or any of the sub-components thereof related to treating a medical ailment/condition for which a course of physical activity is prescribed (e.g., muscle/bone/joint issues, cardiac issues, etc.). As such, prescription 72 will comprise a set of criteria for a desired travel route for the patient. Such criteria can include (among other things) distance, pace, mode of travel (e.g., walking, jogging, running, cycling, etc.), grade/incline of the route, time of day (e.g., for heat and/or night blindness purposes), etc. Thereafter, program 40 will implement a set of rules 78 or the like to perform the underlying functions hereof. Specifically, program 40 will extract the set of criteria from electronic prescription 72. In one embodiment, this can be accomplished by programming set of rules 78 to retrieve certain fields of information from electronic prescription 72. Alternatively, set of rules 72 can cause program 40 to identify keywords or pieces of information in electronic prescription 72.

Regardless, program 40 will then access a database 76 or the like and retrieve information 74 corresponding to a geographical area associated with the patient. Along these lines, information 74 can comprise various maps (street, topographical, etc.) of the geographic area associated with the corresponding patient, weather forecast details, air quality information, pollen counts, etc. This information 74 can initially be determined and stored in database 76 using global positioning satellite (GPS) technology or the like. In any event, program 40 will then identify a set of possible travel routes between a starting point and a destination within the geographical area based on information 74. In general, the starting point and the destination can be provided by the patient, the health care provider, or both. The health care provider may be involved in the designation of these points if he/she would like the patient to maintain a certain distance. Regardless of who designates the points, program 40 will analyze the maps, etc. (included with information 74) to identify all possible travel routes between the stated starting point and destination. Then, program 40 will compare the set of criteria to the information to determine at least one travel route (from the possible travel routes) that is the most appropriate to treat the medical condition. Once one or more appropriate travel routes have been determined, program 40 will provide output 80 with information containing a recommendation thereof.

Figure 3:
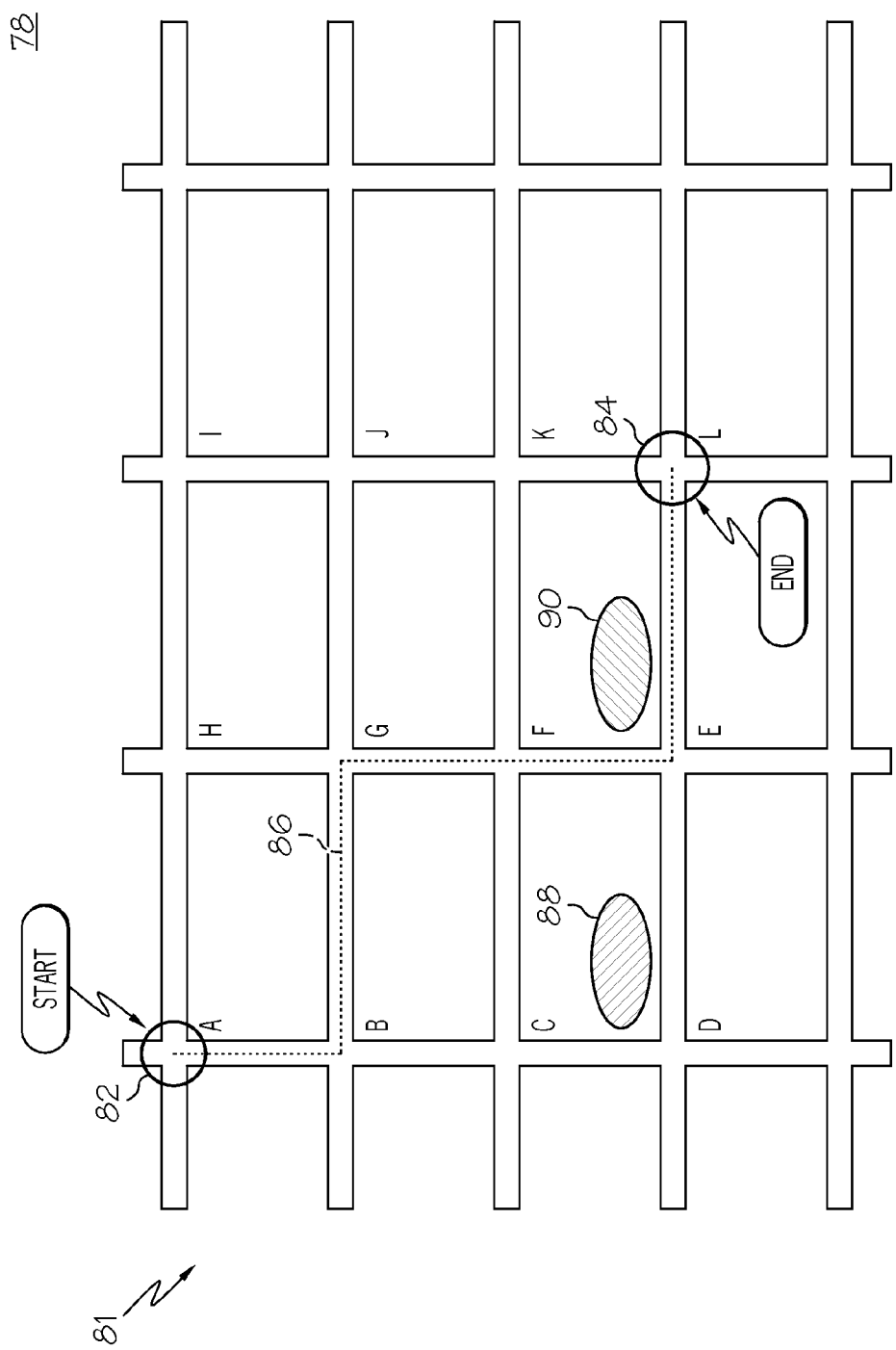
FIG. 3 depicts a graphical illustration of potential travel routes according to an embodiment of the present invention.

Referring now to FIG. 3, illustrative output 80 according to an embodiment of the present invention is shown. As depicted output 80 can comprise a map 80 corresponding to a geographic area associated with the patient. As further shown, map 80 includes a starting point 82 and a destination 84 (e.g., as set by the patient, the health care provider, etc.) and a set of intersections/points denoted by letters "A-L". To travel from starting point 82 to destination 84, the patient can traverse any number of travel routes. However, based on information/details 74 (FIG. 2) about the geographic region as obtained from database 76 (FIG. 2), and the set of criteria set for the prescription by the health care professional, program 40 (FIG. 2) will select the most approximate travel route (e.g., the travel route that provides the closest match of the set of criteria to the geographical area's details/information.

In the example shown, the health care provider is attempting to treat a patient with heart disease and knee problems. As such, the health care provider is prescribing jogging for the patient from the starting point 82 to the destination 84. Moreover, the health care provider would like the patient to perform the jogging along a topographically flat travel route 90 (as opposed to a travel route with hills 88). Program 40 will extract such criteria, compare the same to the details/information for the geographical area, and recommend that the patient traverse a travel route along points "A-B-G-F-E-L." It is understood that this example is intended to be illustrative only and not limiting.

Figure 4:
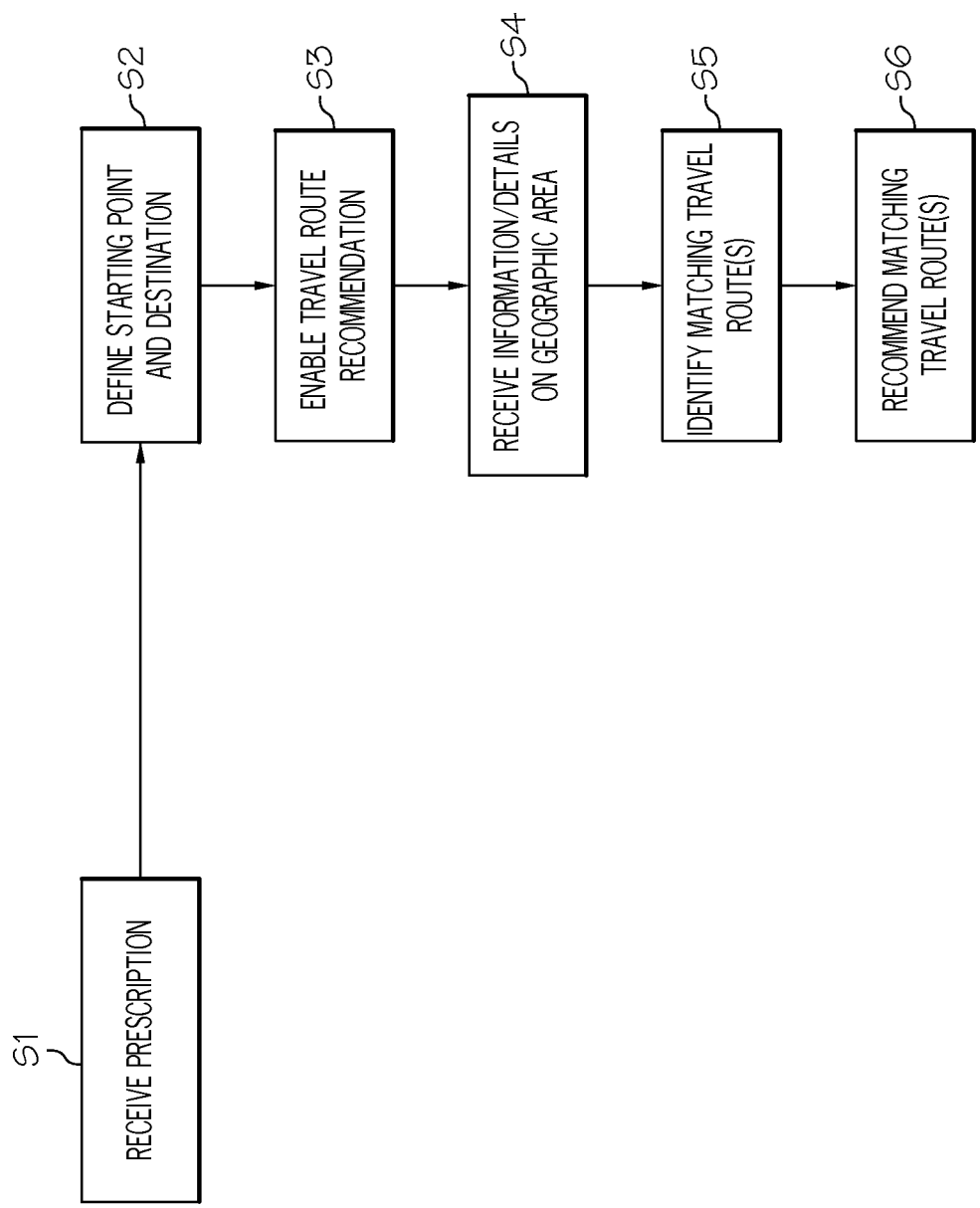
FIG. 4 depicts a method flow diagram according to the present invention.

Referring now to FIG. 4, a method flow diagram according to the present invention is shown. In step S1, a hospital server or the like provides access to a patient's prescription. In step S2, the patient defines a starting point and a destination. In step S3, the patient enables permission for the system to utilize the prescription for travel route recommendation. In step S4, the system receives information related to the geographic area associated with the patient (e.g., maps, road plans, topography, distances, etc.). In step S5, the criteria set forth in the prescription are compared to the information received in step S4 to identify at least one travel route providing the closest match (e.g., that best meets the patient's needs as set forth in the prescription). In step S6, such travel route(s) are recommended to the patient who can then select which (if any) to traverse.

While shown and described herein as a prescription-based travel route recommendation system, it is understood that the invention further provides various alternative embodiments. For example, in one embodiment, the invention provides a computer-readable/useable medium that includes computer program code to enable a computer infrastructure to provide a prescription-based travel route recommendation functionality as discussed herein. To this extent, the computer-readable/useable medium includes program code that implements each of the various processes of the invention. It is understood that the terms computer-readable medium or computer-useable medium comprise one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory 28 (FIG. 1) and/or storage system 34 (FIG. 1) (e.g., a fixed disk, a read-only memory, a random access memory, a cache memory, etc.).

In another embodiment, the invention provides a method that performs the process of the invention on a subscription, advertising, and/or fee basis. That is, a service provider, such as a Solution Integrator, could offer to provide a prescription-based travel route recommendation functionality. In this case, the service provider can create, maintain, support, etc., a computer infrastructure, such as computer system 12 (FIG. 1) that performs the processes of the invention for one or more consumers. In return, the service provider can receive payment from the consumer(s) under a subscription and/or fee agreement and/or the service provider can receive payment from the sale of advertising content to one or more third parties.

In still another embodiment, the invention provides a computer-implemented method for a prescription-based travel route recommendation. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

As used herein, it is understood that the terms "program code" and "computer program code" are synonymous and mean any expression, in any language, code, or notation, of a set of instructions intended to cause a computing device having an information processing capability to perform a particular function either directly or after either or both of the following: (a) conversion to another language, code, or notation; and/or (b) reproduction in a different material form. To this extent, program code can be embodied as one or more of: an application/software program, component software/a library of functions, an operating system, a basic device system/driver for a particular computing device, and the like.

A data processing system suitable for storing and/or executing program code can be provided hereunder and can include at least one processor communicatively coupled, directly or indirectly, to memory elements through a system bus. The memory elements can include, but are not limited to, local memory employed during actual execution of the program code, bulk storage, and cache memories that provide temporary storage of at least some program code in order to reduce the number of times code must be retrieved from bulk storage during execution. Input/output and/or other external devices (including, but not limited to, keyboards, displays, pointing devices, etc.) can be coupled to the system either directly or through intervening device controllers.

Network adapters also may be coupled to the system to enable the data processing system to become coupled to other data processing systems, remote printers, storage devices, and/or the like, through any combination of intervening private or public networks. Illustrative network adapters include, but are not limited to, modems, cable modems, and Ethernet cards.

The foregoing description of various aspects of the invention has been presented for purposes of illustration and description. It is not intended to be exhaustive or to limit the invention to the precise form disclosed and, obviously, many modifications and variations are possible. Such modifications and variations that may be apparent to a person skilled in the art are intended to be included within the scope of the invention as defined by the accompanying claims.

What is claimed is:

1. A computer-implemented method for prescription-based travel route recommendation, comprising:

receiving, from a hospital server, a prescription related to a medical condition of a patient in a computer memory medium, the prescription being issued from a health care provider and comprising a set of criteria for a desired travel route for the patient, the set of criteria comprising, a time of day for traversing the desired travel route and an indication as to whether the travel route should be flat or hilly;

receiving, from the health care provider, a starting point and a destination within a geographical area associated with the patient;

receiving authorization to base a travel route recommendation on the prescription;

receiving topographical information, from a global positioning system, corresponding to the geographical area associated with the patient;

identifying a set of possible travel routes between the starting point and the destination within the geographical area based on the information;

determining at least one travel route from the possible travel routes for treating the medical condition based on a comparison of the set of criteria to the topographical information; and recommending the at least one travel route to the patient.

2. The computer-implemented method of claim 1, the prescription being received by electronic communication from the health care provider.

3. The computer-implemented method of claim 1, the information comprising topographical information pertaining to the geographical area.

4. The computer-implemented method of claim 3, the topographical information being received from using global positioning satellite (GPS) technology.

5. The computer-implemented method of claim 1, the at least one travel route comprising a set of geographical points.

6. A system for a prescription-based travel route recommendation, comprising:

a memory medium comprising instructions;

a bus coupled to the memory medium; and a processor coupled to the bus that when executing the instructions causes the system to:

receive, from a hospital server, a prescription related to a medical condition of a patient in a computer memory medium, the prescription being issued from a health care provider and comprising a set of criteria for a desired travel route for the patient, the set of criteria comprising, a time of day for traversing the desired travel route and an indication as to whether the travel route should be flat or hilly;

receive, from the health care provider, a starting point and a destination within a geographical area associated with the patient;

receive authorization to base a travel route recommendation on the prescription;

receive topographical information, from a global positioning system, corresponding to the geographical area associated with the patient;

identify, by the patient, a set of possible travel routes between the starting point and the destination within the geographical area based on the information;

determine at least one travel route from the possible travel routes for treating the medical condition based on a comparison of the set of criteria to the topographical information; and recommend the at least one travel route to the patient.

7. The system of claim 6, the prescription being received by electronic communication from the health care provider.

8. The system of claim 6, the information comprising topographical information pertaining to the geographical area.

9. The system of claim 8, the topographical information being received from using global positioning satellite (GPS) technology.

10. The computer-implemented method of claim 6, the at least one travel route comprising a set of geographical points.

11. A computer program product for a prescription-based travel route recommendation, the computer program product comprising a computer readable storage media, and program instructions stored on the computer readable storage media, to:

receiving, from a hospital server, a prescription related to a medical condition of a patient in a computer memory medium, the prescription being issued from a health care provider and comprising a set of criteria for a desired travel route for the patient, the set of criteria comprising, a time of day for traversing the desired travel route and an indication as to whether the travel route should be flat or hilly;

receiving, from the health care provider, a starting point and a destination within a geographical area associated with the patient;

receiving authorization to base a travel route recommendation on the prescription;

receive topographical information, from a global positioning system, corresponding to the geographical area associated with the patient;

identify, by the patient, a set of possible travel routes between the starting point and the destination within the geographical area based on the information;

determine at least one travel route from the possible travel routes for treating the medical condition based on a comparison of the set of criteria to the topographical information; and recommend the at least one travel route to the patient.

12. The computer program product of claim 11, the prescription being received by electronic communication from a health care provider.

13. The computer program product of claim 11, the information comprising topographical information pertaining to the geographical area.

14. The computer program product of claim 13, the topographical information being received from using global positioning satellite (GPS) technology.

15. The computer program product of claim 11, the at least one travel route comprising a set of geographical points.

\* \* \* \* \*